(12) United States Patent
Maka et al.

(10) Patent No.: US 11,331,259 B2
(45) Date of Patent: May 17, 2022

(54) SURFACTANT COMPOSITION

(71) Applicant: RITA CORPORATION, Crystal Lake, IL (US)

(72) Inventors: Katherine S. Maka, Inverness, IL (US); Thomas A. Keech, Schaumburg, IL (US); Lauren A. Strohmaier, Genoa, IL (US)

(73) Assignee: RITA CORPORATION, Crystal Lake, IL (US)

( * ) Notice: Subject to any disclaimer, the term of this patent is extended or adjusted under 35 U.S.C. 154(b) by 0 days.

(21) Appl. No.: 16/813,489

(22) Filed: Mar. 9, 2020

(65) Prior Publication Data

US 2020/0206118 A1    Jul. 2, 2020

Related U.S. Application Data

(63) Continuation of application No. 15/628,467, filed on Jun. 20, 2017, now Pat. No. 10,583,073.

(60) Provisional application No. 62/352,555, filed on Jun. 20, 2016.

(51) Int. Cl.

| | |
|---|---|
| *C11D 1/10* | (2006.01) |
| *C11D 1/66* | (2006.01) |
| *C11D 1/86* | (2006.01) |
| *C11D 3/22* | (2006.01) |
| *C11D 1/83* | (2006.01) |
| *A61K 8/60* | (2006.01) |
| *A61K 8/37* | (2006.01) |
| *A61K 8/44* | (2006.01) |
| *A61Q 11/00* | (2006.01) |
| *A61Q 9/02* | (2006.01) |
| *A61Q 5/02* | (2006.01) |
| *A61Q 5/00* | (2006.01) |
| *C11D 1/02* | (2006.01) |
| *C11D 1/88* | (2006.01) |
| *C11D 1/94* | (2006.01) |
| *C11D 3/26* | (2006.01) |
| *C11D 1/37* | (2006.01) |
| *C11D 1/18* | (2006.01) |
| *C11D 3/32* | (2006.01) |
| *C11D 3/34* | (2006.01) |
| *A61Q 19/10* | (2006.01) |
| *C11D 3/20* | (2006.01) |

(52) U.S. Cl.
CPC ............ *A61K 8/604* (2013.01); *A61K 8/37* (2013.01); *A61K 8/44* (2013.01); *A61K 8/442* (2013.01); *A61Q 5/00* (2013.01); *A61Q 5/02* (2013.01); *A61Q 9/02* (2013.01); *A61Q 11/00* (2013.01); *A61Q 19/10* (2013.01); *C11D 1/02* (2013.01); *C11D 1/10* (2013.01); *C11D 1/18* (2013.01); *C11D 1/37* (2013.01); *C11D 1/662* (2013.01); *C11D 1/83* (2013.01); *C11D 1/88* (2013.01); *C11D 1/94* (2013.01); *C11D 3/2079* (2013.01); *C11D 3/22* (2013.01); *C11D 3/222* (2013.01); *C11D 3/26* (2013.01); *C11D 3/32* (2013.01); *C11D 3/34* (2013.01); *A61K 2800/30* (2013.01); *A61K 2800/596* (2013.01)

(58) Field of Classification Search
CPC .... C11D 1/10; C11D 1/18; C11D 1/37; C11D 1/662; C11D 1/83; C11D 1/88; C11D 1/94; C11D 3/22; C11D 3/32; C11D 3/34
USPC ....... 510/123, 124, 126, 130, 136, 137, 138, 510/499, 501, 505, 506
See application file for complete search history.

(56) References Cited

U.S. PATENT DOCUMENTS

| | | |
|---|---|---|
| 5,744,062 A | 4/1998 | Dahms et al. |
| 5,911,981 A | 6/1999 | Dahms et al. |
| 6,025,522 A | 2/2000 | Cox et al. |
| 10,583,073 B2 * | 3/2020 | Maka ..................... A61K 8/604 |
| 2006/0019847 A1 | 1/2006 | Fan et al. |
| 2007/0141012 A1 | 6/2007 | Cho et al. |
| 2008/0139433 A1 | 6/2008 | Mock et al. |
| 2011/0092405 A1 | 4/2011 | Ryklin et al. |
| 2011/0139170 A1 | 6/2011 | Hippe et al. |
| 2012/0021960 A1 | 1/2012 | Wenk et al. |
| 2014/0349902 A1 * | 11/2014 | Allef ..................... A61K 8/361 |
| | | 510/119 |
| 2015/0011449 A1 | 1/2015 | Snyder et al. |
| 2015/0011456 A1 | 1/2015 | Griffin et al. |
| 2015/0038391 A1 | 2/2015 | De Wit et al. |
| 2015/0044157 A1 | 2/2015 | Kulkarni et al. |

(Continued)

FOREIGN PATENT DOCUMENTS

| | | |
|---|---|---|
| EP | 2314270 A2 | 4/2011 |
| EP | 2465840 A1 | 6/2012 |
| FR | 2785800 A1 | 5/2000 |
| KR | 20080110054 A | 12/2008 |
| KR | 101450051 B1 | 10/2014 |

OTHER PUBLICATIONS

"Dual Action Face Wash + Scrub", The Purist Company, from Mintel's Global New Products Database Accession No. 1219822 (Nov. 2009).

(Continued)

*Primary Examiner* — Gregory R Delcotto
(74) *Attorney, Agent, or Firm* — Marshall, Gerstein & Borun LLP

(57) ABSTRACT

A surfactant composition comprising a sugar-based surfactant comprising a C8-C16 alkyl glucoside, a C8-C16 alkyl polyglucoside, or a combination of a C8-C16 alkyl glucoside and a C8-C16 alkyl polyglucoside; a C8-C18 amphodiacetate; a C8-C16 acyl sarcosinate, a C8-C16 acyl glutamate, a C8-C16 acyl glycinate, or a combination thereof; and optionally a C8-C14 acyl lactylate, wherein the composition is free of sulfated anionic surfactants.

7 Claims, No Drawings

(56) References Cited

U.S. PATENT DOCUMENTS

| | | | |
|---|---|---|---|
| 2015/0118172 A1 | 4/2015 | Rudolph et al. | |
| 2015/0157545 A1 | 6/2015 | Rizk | |
| 2015/0225676 A1 | 8/2015 | De Wit et al. | |
| 2015/0297489 A1* | 10/2015 | Kleinen | C11D 1/94 514/785 |
| 2015/0328135 A1* | 11/2015 | Argembeaux | A61Q 19/10 510/119 |
| 2015/0335555 A1 | 11/2015 | Dobrowolski et al. | |
| 2016/0022557 A1* | 1/2016 | Galleguillos | A61Q 5/02 510/123 |
| 2016/0095804 A1 | 4/2016 | Xavier et al. | |

OTHER PUBLICATIONS

"Eucarol AGE EC" Data Sheet, retrieved from the Internet at: <http://cosmetics.specialchem.com/product/i-lamberti-eucarol-age-ec> (Jun. 8, 2016).

"Eucarol AGE ET" Data Sheet, retrieved from the Internet at: <http://cosmetics.specialchem.com/product/i-lamberti-eucarol-age-et> (Jun. 8, 2016).

"Luxurious Shampoo" Product Sheet, Renpure Company, from Mintel's Global New Products Database Accession No. 3060245 (Mar. 2015).

"One Step Cleansing Foam", Amorepacific, Mintel's Global New Products Database Accession No. 2362166 (Apr. 2014).

"Washing Foam", Tokiwa Pharmaceutical Co., from Mintel's Global New Products Database Accession No. 1773487 (Apr. 2012).

International Search Report and Written Opinion, International Application No. PCT/US2017/038320, dated Sep. 11, 2017.

Lamberti, Chemical Specialities, "Eucarol Ages, Natural Based Surfactants," Retrieved: Jun. 20, 2017 <http://www.lamberti.com/products/brochure.cfm?nav=0205> applicant's internal files; admitted prior art).

Stepan®, Product Bulletin, "Amphosol® 2C", Dec. 2012, Retrieved Dec. 2012 http://www.stepan.com/produdt/Surfactants applicant's internal files; admitted prior art).

* cited by examiner

SURFACTANT COMPOSITION

CROSS REFERENCE TO RELATED APPLICATION

This application is a continuation of U.S. patent application Ser. No. 15/628,467, filed Jun. 20, 2017, which claims the benefit under 35 U.S.C. § 119(e) of U.S. provisional patent application Ser. No. 62/352,555, filed Jun. 20, 2016, the entire disclosure of which are incorporated herein by reference, are hereby claimed.

FIELD OF INVENTION

The present disclosure is directed to surfactant compositions, more particularly, to sulfate-free surfactant compositions which are capable of producing stable foam. A method of generating a stable foam is also disclosed.

BACKGROUND OF INVENTION

Foam is an important property of cleaning compositions, especially for personal care compositions, such as hair shampoos, body gels, dentifrices, and shaving creams. Esthetically, foam is an important property because consumers equate a rich, long-lasting foam to a high quality product that works well. Functionally, foam is an important property because the foam first acts as a carrier to deliver cleaning surfactants to the skin or hair, then acts as a carrier to help remove emulsified soil and sebum from the cleaned skin or hair.

However, to achieve these esthetic and functional goals, the foam must be present in a wet, or spherical, form. If the generated foam is unstable, the foam changes from the wet form to the dry, or hexagonal, form relatively quickly, i.e., in less than about two minutes. Dry foam bubbles break quickly, and, therefore, for dermatogically preferred compositions do not provide the esthetic and functional foam properties typically required for consumer acceptance of the composition.

Foam is created by dispersing air or a gas in a surfactant-containing liquid. The mechanism of dispersing a gas in a surfactant-containing liquid is similar to the dispersion of two immiscible liquids during formation of an emulsion. Consequently, gas bubbles dispersed in a liquid are stabilized in the same manner as emulsions, i.e., by formation of surfactant layers at the gas-liquid interface. The surfactant layers keep the gas bubbles separated and prevent "coalescence," i.e., the merging of small gas bubbles to form larger gas bubbles. In general, more dense and more compact surfactant layers form smaller bubbles and retard the coalescence mechanism.

It is well known that because of the very large density difference between the dispersed gas and the liquid, the gas bubbles rise to the top of the liquid. The enriched concentration of gas bubbles at the top of the liquid appear as "foam." Initially, all of the gas bubbles in the foam are spherical, there is sufficient space between each individual spherical gas bubble for the presence of the surfactant-containing liquid, and the foam behaves like an emulsion. Such a foam is termed a "wet foam."

Over time, the liquid present in the interstices between the individual gas bubbles drains out due to gravity. Depending on the nature and chemical structure of the surfactant in the liquid, lamellar liquid crystalline layers form and arrange at the gas-liquid interface. If the lamellar layers have a low viscosity, the surfactant-containing liquid between individual gas bubbles can drain relatively easily, and the spherical form of the foam bubbles can change into a hexagonal form relatively quickly. Hexagonal bubbles quickly break. The transition of a foam from the spherical form to the hexagonal form due to foam aging can be observed visually. Foam in the hexagonal form is termed a "dry foam." Dry foams are unstable, which leads to a rapid reduction in foam volume due to rapidly breaking bubbles.

However, if the lamellar surfactant layers have a relatively higher viscosity, the transition from a spherical foam to the hexagonal form can be delayed. The speed of the transition of a foam from the spherical to hexagonal form determines how the foam is used in practical applications, and also determines how the foam is perceived esthetically. For example, for shampoos and shower gels, foams having a foam transition of about two minutes or less, i.e., a metastable foam structure, is desirable. Foam stability is controlled by many factors associated with the physiochemical properties of the surfactant solution such as surface tension, film surface tension (lamellar foams), surface viscosity and elasticity amongst others. A more stable foam could lead to insufficient wetting and distribution of the surfactant on the skin or hair, because during application of the shampoo or shower gel to the skin or hair, some parts of that foam undergo the transition to hexagonal state that allows the surfactant to drain from between the bubbles to contact and wet the hair or skin. Then, by continual rubbing of the shampoo or shower gel on the skin or hair, new foam bubbles are generated, which act as a carrier to lift and remove soil and sebum from the skin or hair and additional water rinses it off. Esthetically, spherical foam is desired. Functionally, the transition to the hexagonal form and regeneration of the spherical foam provides cleansing.

Other foam applications, e.g., shaving foams, require a foam having a much greater stability because the applied foam is not regenerated by continual rubbing techniques and because of the relatively long time required to complete the entire shaving operation. Furthermore, a controlled and sufficient wetting of the hair and skin is required for a smooth shaving operation. Sufficient wetting when a surfactant is foamed occurs only if the surfactant-containing liquid can drain from the foam lamellae to contact the skin, and drainage occurs more readily when the foam bubbles are in the spherical form.

The difference in structure between a wet, spherical foam and a dry, hexagonal foam is illustrated in FIGS. 3 and 4 of U.S. Pat. No. 5,911,811. FIG. 3 of U.S. Pat. No. 5,911,811 clearly shows both the lamellar liquid crystalline surfactant structure that stabilizes each bubble of a wet foam and the large amount of surfactant-containing liquid between individual bubbles. The relatively thick surfactant structure illustrated in FIG. 3 also retards the coalescence of neighboring bubbles into a single, larger bubble. In contrast, FIG. 4 of U.S. Pat. No. 5,911,811 shows a lack of a stabilizing surfactant structure around the hexagonal bubbles and the relative absence of surfactant-containing liquid between the bubbles.

The most commonly used sulfated anionic surfactants are well known for providing a high volume of a stable foam and having an excellent ability to emulsify soils and oils, i.e., to act as an efficient cleaner of skin and hair. Sulfated anionic surfactants include the anionic sulfates and the anionic sulfonates. As a result of these properties, sulfated anionic surfactants have been the primary surfactant used in shampoos and other skin and hair cleaning products. However, sulfated anionic surfactants have disadvantages. For example, the sulfated anionic surfactants strip the hair of natural oils that condition the hair and thereby can damage the hair and give freshly shampooed hair a dry feel. Sulfated anionic surfactants also are harsh to the skin and eyes, and thus sulfated anionic surfactants are generally unsuitable for use in baby shampoos and pet products.

Amphoteric and nonionic surfactants are relatively mild to the skin and eyes and do not strip the hair of natural oils. However, amphoteric and nonionic surfactants typically generate a poor foam in comparison to a sulfated anionic surfactant. Therefore, shampoos and similar cleaners based primarily on amphoteric and nonionic surfactants have not achieved good consumer acceptance. But, amphoteric and nonionic surfactants have been used in conjunction with sulfated anionic surfactants in attempts to provide a shampoo that takes advantage of the foaming properties of a sulfated anionic surfactant, while tempering the disadvantageous properties of the sulfated anionic surfactant with a nonionic or amphoteric surfactant.

DETAILED DESCRIPTION

The disclosure provides sulfate-free surfactant compositions that are capable of producing a stable foam that remain in the wet, or spherical, form for at least as long as a comparable sulfate-based product. Beneficially, the disclosed surfactant compositions are free of sulfated anionic surfactants. Further, the disclosed surfactant compositions do not cause adverse reactions and thus are suitable for a number of uses including but not limited to applications where a milder surfactant composition may be desired such as in baby shampoos and pet products. Thus, the surfactant compositions according to the disclosure are free of lauryl ether sulfates, lauryl sulfates, and sulfonates. In the context of this disclosure, the term "free of sulfated anionic surfactants" means that a sulfated anionic surfactant is not intentionally added to a surfactant composition according to the disclosure, but may be present as a by-product or contaminant such that a surfactant composition according to the disclosure may contain 0% to about 0.1% by weight of a sulfated anionic surfactant.

In one embodiment, the disclosure provides a surfactant composition comprising a sugar-based surfactant comprising a C8-C16 alkyl glucoside, a C8-C16 alkyl polyglucoside, or a combination of a C8-C16 alkyl glucoside and a C8-C16 alkyl polyglucoside; a C8-C18 amphodiacetate; a C8-C16 acyl sarcosinate, a C8-C16 acyl glutamate, a C8-C16 acyl glycinate, or a combination thereof; and optionally a C8-C14 acyl lactylate, wherein the composition is free of sulfated anionic surfactants.

In another embodiment, the disclosure provides a method of generating a stable, wet foam comprising adding a surfactant blend according to the disclosure to an aqueous composition to provide an aqueous mixture, and forming bubbles from the aqueous mixture of step to generate the stable, wet foam.

The sugar-based surfactant comprising at least one of a C8-C16 alkyl glucoside and/or a C8-C16 alkyl polyglucoside is typically a non-ionic sugar-based (i.e., glucose-based) surfactant but may also be a salt of a sugar-based surfactant. The sugar-based surfactant may be present in the surfactant compositions according to the disclosure in an amount between about 10 weight percent (wt. %) and about 40 wt. %, between about 15 wt. % and about 35 wt. %, and/or between 20 wt. % and about 30 wt. %. The sugar-based surfactant can be prepared/derived from the 6-carbon monosaccharide glucose and C8-C16 alcohols. Suitable C8-C16 alkyl glucosides include but are not limited to: decyl glucoside, heptyl glucoside, octyl glucoside, lauryl glucoside (or dodecyl glucoside), coco-glucosides (which is a mixture of C8-C16 alkyl glucosides), and combinations thereof. Suitable C8-C16 alkyl polyglucosides include but are not limited to: disodium coco-glucoside citrate, sodium coco-glucoside tartrate, and combinations thereof. Combinations of one or more C8-C16 alkyl glucosides and one or more C8-C16 alkyl polyglucosides may also be used. In one aspect, the sugar-based surfactant is the primary surfactant in the composition, i.e., the sugar-based surfactant is present in an amount greater than any other surfactant in the composition.

The C8-C18 acyl amphodiacetate typically serves as a secondary surfactant and a foam booster in the surfactant compositions according to the disclosure. The C8-C18 acyl amphodiacetate may be prepared by procedures including a step in which aminoethylethanolamine is reacted with fatty acyl compounds. The C8-C18 acyl amphodiacetate is an amphoteric surfactant typically having the following formula (I):

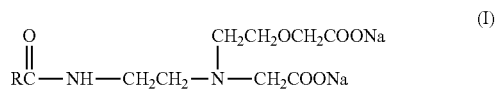

wherein R may be C8-C18 alkyl or C8-C18 alkenyl. While the amphodiacetate of formula (I) includes sodium as the counter ion, other alkaline metals may also be used. The C8-C18 acyl amphodiacetate may be present in the surfactant compositions according to the disclosure in an amount between about 5 weight percent (wt. %) and about 25 wt. %, between about 10 wt. % and about 20 wt. %, and/or between 12 wt. % and about 18 wt. %. Suitable C8-C18 acyl amphodiacetates include but are not limited to: capryl amphodiacetate, lauryl amphodiacetate (or dodecyl amphodiacetate), cocoamphodiacetate (which is a mixture of C8-C16 acyl amphodiacetates), and combinations thereof.

The C8-C16 acyl sarcosinate, C8-C16 acyl glutamate, and/or C8-C16 acyl glycinate is an anionic surfactant derived from the amino acid sarcosine, glutamine, or glycine, respectively, and a corresponding C8-C16 fatty acid. The C8-C16 acyl sarcosinate, C8-C16 acyl glutamate, and/or C8-C16 acyl glycinate may be present in the surfactant compositions according to the disclosure in an amount between about 10 weight percent (wt. %) and about 35 wt. %, between about 15 wt. % and about 30 wt. %, and/or between 20 wt. % and about 25 wt. %. Suitable C8-C16 acyl sarcosinates include but are not limited to: sodium lauroyl sarcosinate, sodium cocoyl sarcosinate (which is a mixture of sodium C8-C16 acyl sarcosinates), sodium myristoyl sarcosinate, ammonium lauroyl sarcosinate, ammonium cocoyl sarcosinate, isopropyl lauroyl sarcosinate, potassium cocoyl sarcosinate, potassium lauroyl sarcosinate, and combinations thereof; suitable C8-C16 acyl glutamates include but are not limited to: sodium lauroyl glutamate, sodium cocoyl glutamate (which is a mixture of sodium C8-C16 acyl glutamates), sodium myristoyl glutamate, ammonium lauroyl glutamate, ammonium cocoyl glutamate, isopropyl lauroyl glutamate, potassium cocoyl glutamate, potassium lauroyl glutamate, and combinations thereof; suitable C8-C16 acyl glycinates include but are not limited to: sodium lauroyl glycinate, sodium cocoyl glycinate (which is a mixture of sodium C8-C16 acyl glycinates), sodium myristoyl glycinate, ammonium lauroyl glycinate, ammonium cocoyl glycinate, isopropyl lauroyl glycinate, potassium cocoyl glycinate, potassium lauroyl glycinate, and combinations thereof. Combinations of one or more C8-C16 acyl sarcosinates, C8-C16 acyl glutamates, and/or C8-C16 acyl glycinates may also be used. For example, a combination of one or more C8-C16 acyl sarcosinate and one or more C8-C16 acyl glycinate may be used. Similarly, for example, a combination of one or more C8-C16 acyl sarcosinate and one or more C8-C16 acyl glutamate may be used. Combinations of one or more C8-C16 acyl sarcosinate, one or more C8-C16 acyl glutamate, and one or more C8-C16 acyl glycinate also may be used.

The C8-C14 acyl lactylate is an anionic surfactant that typically serves as a foam booster and viscosity enhancer in the surfactant compositions according to the disclosure. The combination of the C8-C14 acyl lactylate with the other components of the surfactant combinations, in particular with the sugar-based surfactant comprising a C8-C14 alkyl glucoside, has been found to be particularly effective for enhancing foam quality. The C8-C14 acyl lactylate may be present in the surfactant compositions according to the disclosure in an amount between about 0 weight percent (wt. %) and about 10 wt. %, between about 0 wt. % and about 7.5 wt. %, and/or between 1 wt. % and about 4 wt. %. The C8-C14 acyl lactylate can be prepared by reacting a C8-C14 fatty acid with lactic acid. Suitable C8-C14 acyl lactylates include but are not limited to: sodium caproyl lactylate, sodium lauroyl lactylate, sodium myristoyl lactylate, and combinations thereof. Of course, ammonium and potassium salts may also be used.

The surfactant compositions according to the disclosure may optionally contain other foam booster and/or viscosity enhancers including but not limited to surfactants encompassing betaine and sultaine classes, specifically, C8-C16 betaine surfactants such as capryl betaine, decyl betaine, lauryl betaine, myristyl betaine, and C8-C16 sultaine surfactants such as cocamidopropyl sultaine, capryl sultaine, decyl sultaine, lauryl sultaine, myristyl sultaine, coco sultaine, cocamidopropyl hydroxysultaine, capryl hydroxysultaine, decyl hydroxysultaine, lauryl hydroxysultaine, myristyl hydroxysultaine, coco hydroxysultaine, and mixtures of the foregoing betaine and sultaine surfactants.

In various embodiments, the surfactant compositions may contain from about 15 wt. % to about 55 wt. %, about 25 wt. % to about 45 wt. %, and/or about 30 wt. % to about 40 wt. % of water.

Preservatives and/or biocides may also be included in the surfactant compositions.

In various preferred embodiments, the surfactant compositions according to the disclosure are free of one or more of diethanolamines, monoethanol amines, and/or parabens (parahydroxybenzoates). In a particularly preferred embodiment, the surfactant compositions according to the disclosure are free of diethanolamines, monoethanol amines, and parabens (parahydroxybenzoates).

The surfactant compositions according to the disclosure may be used in a number of different personal care compositions. In particular, the surfactant compositions according to the disclosure can be incorporated into shaving foams, dentrifices, shampoos, shower gels, soaps (both liquid and bars; hand washes; body washes), and hair care foams such as mousses and dyes.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

In addition, uses of "a" or "an" are employed to describe elements and components of the embodiments described herein. This is done merely for convenience and to give a general sense of the description. This description, and the claims that follow, should be read to include one or at least one, and the singular also includes the plural unless it is clear that it is meant otherwise.

Although the foregoing text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Example 1

A surfactant composition according to the disclosure was prepared by combining lauryl glucoside, sodium lauroyl lactylate, sodium lauroyl sarcosinate, disodium cocoamphodiacetate, and water in the amounts shown in Table 1.

TABLE 1

| Raw Material | amount (wt. %) |
| --- | --- |
| Lauryl Glucoside | 25.00 |
| Sodium Lauroyl Lactylate | 2.50 |
| Sodium Lauroyl Sarcosinate | 22.00 |
| Disodium Cocoamphodiacetate | 15.00 |
| Water | 35.50 |

The surfactant compositions were found to have excellent foaming properties comparable or better than a leading brand sulfate based shampoo ("sulfated benchmark") and to cause no irritation.

What is claimed is:

1. A surfactant composition comprising:
   lauryl glucoside in an amount between about 10 weight percent (wt. %) and about 40 wt. %, based on the total weight of the composition;
   disodium cocoamphodiacetate;
   sodium lauroyl sarcosinate in an amount between about 20 weight percent (wt. %) and about 35 wt. %, based on the total weight of the composition; and,
   sodium lauroyl lactylate,
   wherein the composition is free of sulfated anionic surfactants, free of a sultaine, and free of a betaine.

2. The surfactant composition according to claim 1, wherein the lauryl glucoside is the primary surfactant in the composition.

3. The surfactant composition according to claim 1, wherein the cocoamphodiacetate is present in an amount between about 5 weight percent (wt. %) and about 25 wt. %, based on the total weight of the composition.

4. The surfactant composition according to claim 1, wherein the sodium lauroyl lactylate is present in an amount up to about 10 wt. %, based on the total weight of the composition.

5. The surfactant composition according to claim 1, wherein the surfactant compositions comprises from about 15 wt. % to about 55 wt. % of water, based on the total weight of the composition.

6. The surfactant composition according to claim 1, wherein the surfactant composition is free of one or more of diethanolamines, monoethanol amines, and/or parabens.

7. The surfactant composition according to claim 1, wherein the surfactant composition is free of each of diethanolamines, monoethanol amines, and parabens.

\* \* \* \* \*